United States Patent
Dolhun

(10) Patent No.: US 8,557,301 B2
(45) Date of Patent: Oct. 15, 2013

(54) ORAL REHYDRATION COMPOSITION

(75) Inventor: Eduardo P. Dolhun, San Francisco, CA (US)

(73) Assignee: Drip Drop, Inc., San Francisco, CA (US)

( * ) Notice: Subject to any disclaimer, the term of this patent is extended or adjusted under 35 U.S.C. 154(b) by 0 days.

(21) Appl. No.: 13/175,705

(22) Filed: Jul. 1, 2011

(65) Prior Publication Data

US 2013/0004594 A1    Jan. 3, 2013

(51) Int. Cl.
*A01N 59/00*    (2006.01)
*A01N 59/08*    (2006.01)
*A01N 43/04*    (2006.01)
*A01N 61/00*    (2006.01)
*A61K 33/00*    (2006.01)
*A61K 33/14*    (2006.01)
*A61K 9/14*    (2006.01)
*A61K 31/70*    (2006.01)
*A61K 31/00*    (2006.01)

(52) U.S. Cl.
USPC ........... 424/722; 424/600; 424/663; 424/680; 424/489; 514/23; 514/837; 514/867

(58) Field of Classification Search
None
See application file for complete search history.

(56) References Cited

U.S. PATENT DOCUMENTS

| 5,100,677 | A | * | 3/1992 | Veech ........................... 424/677 |
| 5,397,786 | A | | 3/1995 | Simone |
| 5,891,888 | A | | 4/1999 | Strahl |
| 6,596,702 | B2 | | 7/2003 | Kampinga et al. |
| 7,375,089 | B2 | | 5/2008 | Verlaan et al. |
| 7,566,463 | B2 | | 7/2009 | Ayala et al. |
| 2007/0160683 | A1 | | 7/2007 | Johnson et al. |
| 2009/0017167 | A1 | * | 1/2009 | Krumhar et al. ................. 426/72 |
| 2009/0148566 | A1 | | 6/2009 | Murray et al. |
| 2010/0104663 | A1 | * | 4/2010 | Collin ........................... 424/678 |

OTHER PUBLICATIONS

Moenginah et al, Tropical Pediatrics and Environmental Child Health, Jun. 1978, pp. 127-130.*
Guerrant et al, Clinical Infectious Disorders, Aug. 2003, vol. 37, pp. 398-405.*
Bahl, R., et al., Reduced-osmolarity oral rehydration salts solution multicentre trial: implications for national policy Indian J Pediatr. Jul.-Aug. 1996;63(4):473-6.
Bhan M.K., et al., Clinical trials of improved oral rehydration salt formulations: a review, Bull World Health Organ, 1994;72(6):945-55.
Black, R.E., et al., Glucose vs sucrose in oral rehydration solutions for infants and young children with rotavirus-associated diarrhea, Pediatrics, Jan. 1981;67(1):79-83.
Chatterjee, A., et al., Evaluation of a sucrose/electrolyte solution for oral rehydration in acute infantile diarrhoea, Lancet, Jun. 25, 1977;1(8026):1333-5.
Chowdhury, A.M.R., et al. Oral Rehydration Therapy: A Community Trial Comparing the Acceptability of Homemade Sucrose and Cereal-Based Solutions, Bull. World Health Org. 69(2):229-234 (1191).
Cleghorn G.J., et al., Comparison of two oral rehydration solutions in children with gastroenteritis in Australia, Clin Ther, 1990;12 Suppl A:81-5.
Costa, A.D., et al., Oral rehydration therapy in emergency departments, J Pediatr (Rio J), Mar.-Apr. 2011;87(2):175-9.
da Cunha Ferreira R.M., Optimising oral rehydration solution composition for the children of Europe: clinical trials, Acta Paediatr Scand Suppl, 1989;364:40-50.
Dias J.A., et al., Improving the palatability of oral rehydration solutions has implications for salt and water transport: a study in animal models, J Pediatr Gastroenterol Nutr, Oct. 1996;23(3):275-9.
Elliott, E.J., et al., *Search for the ideal oral rehydration solution: studies in a model of secretory diarrhoea Gut*, Nov. 1991;32(11):1314-20.
El-Mougi M. 'Efficacy of standard glucose-based and reduced-osmolarity maltodextrin-based oral rehydration solutions: effect of sugar malabsorption' Bull World Health Organ. 1996;74(5):471-7.
Farugue, A.S., et al., Hypo-osmolar sucrose oral rehydration solutions in acute diarrhoea: a pilot study, Acta Paediatr, Oct. 1996;85(10):1247-8.
Fujisawa, T., et al., Intestinal absorption of fructose in the rat, Gastroenterology, Aug. 1991;101(2):360-7.
Hahn, S., et al., Reduced osmolarity oral rehydration solution for treating dehydration due to diarrhoea in children: systematic review, BMJ, Jul. 14, 2001;323(7304):81-5.
Hahn, S., et al. 'Reduced osmolarity oral rehydration solution for treating dehydration caused by acute diarrhoea in children (Review)' [online] 2009 [retrieved on May 18, 2011] Retrieved from the Internet: <URL: http://onlinelibrary.wiley.com/doi/10.1002/14651858.CD002847/abstract.
Khan, A.M., et al., Low osmolar oral rehydration salts solution in the treatment of acute watery diarrhoea in neonates and young infants: a randomized, controlled clinical trial, J Health Popul Nutr. Mar. 2005;23(1):52-7.
Mathew J.L., Non-glucose oral rehydration solution does it make a good thing better?, Indian Pediatr, Jun. 2009;46(6):501-5.
Moenginah, P.A., et al., Sucrose electrolyte solution for oral rehydration in diarrhea, J Trop Pediatr Environ Child Health, Jun. 1978;24(3):127-30.

(Continued)

*Primary Examiner* — Cherie M Stanfield
*Assistant Examiner* — Mark V Stevens
(74) *Attorney, Agent, or Firm* — Wilson, Sonsini, Goodrich & Rosati

(57) ABSTRACT

Disclosed are oral rehydration compositions with sucrose, sodium, chloride, and citric acid or citrate. The composition further comprises an osmolarity of below 250 mOsm/L, and sodium below 75 meq/L. Further disclosed are methods of treatment using the same.

14 Claims, No Drawings

(56) References Cited

OTHER PUBLICATIONS

Pulungsih S.P., et al., Standard WHO-ORS versus reduced-osmolarity ORS in the management of cholera patients, J Health Popul Nutr, Mar. 2006;24(1):107-12.

Rehrer N.J., Fluid and electrolyte balance in ultra-endurance sport, Sports Med, 2001;31(10):701-15.

Richards, L., et al., Management of acute diarrhea in children: lessons learned, Pediatr Infect Dis J. Jan. 1993;12(1):5-9.

Sachdev H.P. Oral rehydration therapy, J Indian Med Assoc, Aug. 1996;94(8):298-305.

Stanton, B. 'Oral rehydration therapy' [online] Jan. 2011 [retrieved Jun. 21, 2011] Retrieved from the Internet: <URL:http://www.uptodate.com/contents/oral-rehydration-therapy.

Suh, J.S., et al., Recent Advances of Oral Rehydration Therapy (ORT), Electrolyte Blood Press, Dec. 2010;8(2):82-6. Epub Dec. 31, 2010.

Telmesani, A.M., Oral rehydration salts, zinc supplement and rota virus vaccine in the management of childhood acute diarrhea, J Family Community Med, May 2010;17(2):79-82.

Uchendu, U.O., et al., Pre-hospital management of diarrhoea among caregivers presenting at a tertiary health institution: implications for practice and health education, Afr Health Sci, Mar. 2011;11(1):41-7.

Varavithya W., Oral rehydration therapy for invasive diarrhea, Rev Infect Dis, Mar.-Apr. 1991;13 Suppl 4:S325-31.

Wall C.R., et al., Osmolality electrolyte and carbohydrate type and oral rehydration solutions: a controlled study to compare the efficacy of two commercially available solutions (osmolalities 240 mmol/L and 340 mmol/L), J Diarrhoeal Dis Res, Dec. 1993;11(4):222-6.

'Carbohydrates and electrolytes (systemic)' [online] [retrieved on Jun. 28, 2011] Retrieved from the Internet: <URL:http://www.drugs.com/mmx/pedialyte.html.

'Military kits, hydration, and ORS administration' [online] vol. 9, No. 17, 2009 Retrieved from the Internet: <URL: http://www.ceraproductsinc.com/research/newsletters_cerasport.html.

'Oral Rehydration Salts (ORS)' [online] [retrieved on Jun. 2, 2011] Retrieved from the Internet: <URL: http://rehydrate.org/ors/expert-consultation.html.

'Oral Rehydration Therapy (ORT) for Diarrhea' [online] [retrieved on Jun. 16, 2011] Retrieved from the Internet: <URL: http://www.childrensmercy.org/content/view.aspx?id=381.

Ansaldi et al. Importance of Oral Rehydration in Acute Infantile Diarrhea: Comparison of 2 Rehydration Solutions. *Minerva Pediatr.*, Jan.-Feb. 1990, 42(1-2):9-14.

PCT/US2011/042860 International Search Report mailed Apr. 6, 2012.

* cited by examiner

ORAL REHYDRATION COMPOSITION

BACKGROUND OF THE INVENTION

Dehydration is the excessive loss of body fluid, accompanied with electrolyte disturbances. There are three types of dehydration: hypotonic or hyponatremic (primarily a loss of electrolytes, sodium in particular), hypertonic or hypernatremic (primarily a loss of water), and isotonic or isonatremic (equal loss of water and electrolytes). Isotonic dehydration is the most common form of dehydration.

SUMMARY OF THE INVENTION

Disclosed herein, in certain embodiments, is an oral rehydration composition, comprising: (a) at least 25% w/w sucrose; (b) between 1% w/w and 12.5% w/w sodium; (c) between 0.1% w/w and 2.5% w/w chloride; (d) between 0.5% w/w and 1% w/w potassium; and (e) e) between 10% w/w and 40% w/w citric acid or citrate; wherein, the composition comprises less than 0.5% glucose, wherein the ratio of sodium to chloride is at least 1.5:1, and wherein the composition has an osmolarity of less than 250 mOsm/L when mixed with water. In some embodiments, the composition comprises at least 40% w/w sucrose. In some embodiments, the composition comprises between 3% w/w sodium and 5% w/w sodium. In some embodiments, the composition comprises less than 0.5% w/w chloride. In some embodiments, the composition comprises a ratio of sodium to chloride of at least 1.5:1. In some embodiments, the composition has an osmolarity less than 250 mOsm/L when mixed with water. In some embodiments, the composition comprises about 1400 mmol/L sucrose. In some embodiments, the composition comprises between 1% w/w sodium and 3.5% w/w sodium. In some embodiments, the composition comprises between 50 meq/L sodium and 70 meq/L sodium. In some embodiments, the composition comprises between 0.1% w/w chloride and 0.7% w/w chloride. In some embodiments, the composition comprises between 0.1% w/w chloride and 0.66% w/w chloride. In some embodiments, the composition comprises between 3 meq/L chloride and 5 meq/L chloride. In some embodiments, the composition comprises a ratio of sodium to chloride of 7:1. In some embodiments, the composition has an osmolarity between 230 mOsm/L and 240 mOsm/L. In some embodiments, the composition comprises less than 0.1% glucose. In some embodiments, the composition comprises less than 20% fructose. In some embodiments, the amount of sodium does not equal the amount of glucose. In some embodiments, the composition comprises between 20% w/w citric acid or citrate and 30% w/w citric acid or citrate.

Disclosed herein, in certain embodiments, is an oral rehydration composition for use in treating or preventing dehydration, comprising: (a) at least 25% w/w sucrose, and (b) at least one electrolyte. In some embodiments, the composition comprises at least 40% w/w sucrose. In some embodiments, the composition comprises between 3% w/w sodium and 5% w/w sodium. In some embodiments, the composition comprises less than 0.5% w/w chloride. In some embodiments, the composition comprises a ratio of sodium to chloride of at least 1.5:1. In some embodiments, the composition has an osmolarity less than 250 mOsm/L when mixed with water. In some embodiments, the composition comprises about 1400 mmol/L sucrose. In some embodiments, the composition comprises between 1% w/w sodium and 3.5% w/w sodium. In some embodiments, the composition comprises between 50 meq/L sodium and 70 meq/L sodium. In some embodiments, the composition comprises between 0.1% w/w chloride and 0.7% w/w chloride. In some embodiments, the composition comprises between 0.1% w/w chloride and 0.66% w/w chloride. In some embodiments, the composition comprises between 3 meq/L chloride and 5 meq/L chloride. In some embodiments, the composition comprises a ratio of sodium to chloride of 7:1. In some embodiments, the composition has an osmolarity between 230 mOsm/L and 240 mOsm/L. In some embodiments, the composition comprises less than 0.1% glucose. In some embodiments, the composition comprises less than 20% fructose. In some embodiments, the amount of sodium does not equal the amount of glucose. In some embodiments, the composition comprises between 20% w/w citric acid or citrate and 30% w/w citric acid or citrate.

Disclosed herein, in certain embodiments, is an oral rehydration composition for use in treating or preventing dehydration, comprising: (a) a carbohydrate; and (b) less than 12.5% w/w of sodium. In some embodiments, the composition comprises at least 40% w/w sucrose. In some embodiments, the composition comprises between 3% w/w sodium and 5% w/w sodium. In some embodiments, the composition comprises less than 0.5% w/w chloride. In some embodiments, the composition comprises a ratio of sodium to chloride of at least 1.5:1. In some embodiments, the composition has an osmolarity less than 250 mOsm/L when mixed with water. In some embodiments, the composition comprises about 1400 mmol/L sucrose. In some embodiments, the composition comprises between 1% w/w sodium and 3.5% w/w sodium. In some embodiments, the composition comprises between 50 meq/L sodium and 70 meq/L sodium. In some embodiments, the composition comprises between 0.1% w/w chloride and 0.7% w/w chloride. In some embodiments, the composition comprises between 0.1% w/w chloride and 0.66% w/w chloride. In some embodiments, the composition comprises between 3 meq/L chloride and 5 meq/L chloride. In some embodiments, the composition comprises a ratio of sodium to chloride of 7:1. In some embodiments, the composition has an osmolarity between 230 mOsm/L and 240 mOsm/L. In some embodiments, the composition comprises less than 0.1% glucose. In some embodiments, the composition comprises less than 20% fructose. In some embodiments, the amount of sodium does not equal the amount of glucose. In some embodiments, the composition comprises between 20% w/w citric acid or citrate and 30% w/w citric acid or citrate.

Disclosed herein, in certain embodiments, is an oral rehydration composition for use in treating or preventing dehydration, comprising: (a) a carbohydrate; and (b) less than 0.5% w/w chloride. In some embodiments, the composition comprises at least 40% w/w sucrose. In some embodiments, the composition comprises between 3% w/w sodium and 5% w/w sodium. In some embodiments, the composition comprises less than 0.5% w/w chloride. In some embodiments, the composition comprises a ratio of sodium to chloride of at least 1.5:1. In some embodiments, the composition has an osmolarity less than 250 mOsm/L when mixed with water. In some embodiments, the composition comprises about 1400 mmol/L sucrose. In some embodiments, the composition comprises between 1% w/w sodium and 3.5% w/w sodium. In some embodiments, the composition comprises between 50 meq/L sodium and 70 meq/L sodium. In some embodiments, the composition comprises between 0.1% w/w chloride and 0.7% w/w chloride. In some embodiments, the composition comprises between 0.1% w/w chloride and 0.66% w/w chloride. In some embodiments, the composition comprises between 3 meq/L chloride and 5 meq/L chloride. In some embodiments, the composition comprises a ratio of sodium to chloride of 7:1. In some embodiments, the composition has an osmolarity between 230 mOsm/L and 240 mOsm/L. In some embodiments, the composition comprises less than 0.1% glucose. In some embodiments, the composition comprises less than 20% fructose. In some embodiments, the amount of sodium does not equal the amount of glucose. In some embodiments, the composition comprises between 20% w/w citric acid or citrate and 30% w/w citric acid or citrate.

Disclosed herein, in certain embodiments, is an oral rehydration composition for use in treating or preventing dehydration, comprising: (a) a carbohydrate; and (b) a ratio of sodium to chloride is at least 1.5:1. In some embodiments, the composition comprises at least 40% w/w sucrose. In some embodiments, the composition comprises between 3% w/w sodium and 5% w/w sodium. In some embodiments, the composition comprises less than 0.5% w/w chloride. In some embodiments, the composition comprises a ratio of sodium to chloride of at least 1.5:1. In some embodiments, the composition has an osmolarity less than 250 mOsm/L when mixed with water. In some embodiments, the composition comprises about 1400 mmol/L sucrose. In some embodiments, the composition comprises between 1% w/w sodium and 3.5% w/w sodium. In some embodiments, the composition comprises between 50 meq/L sodium and 70 meq/L sodium. In some embodiments, the composition comprises between 0.1% w/w chloride and 0.7% w/w chloride. In some embodiments, the composition comprises between 0.1% w/w chloride and 0.66% w/w chloride. In some embodiments, the composition comprises between 3 meq/L chloride and 5 meq/L chloride. In some embodiments, the composition comprises a ratio of sodium to chloride of 7:1. In some embodiments, the composition has an osmolarity between 230 mOsm/L and 240 mOsm/L. In some embodiments, the composition comprises less than 0.1% glucose. In some embodiments, the composition comprises less than 20% fructose. In some embodiments, the amount of sodium does not equal the amount of glucose. In some embodiments, the composition comprises between 20% w/w citric acid or citrate and 30% w/w citric acid or citrate.

Disclosed herein, in certain embodiments, is a method of treating or preventing dehydration in a subject in need thereof, comprising administering to the subject a composition of any preceding claim. In some embodiments, the subject is an athlete. In some embodiments, the subject is a child. In some embodiments, the subject is suffering from diarrhea. In some embodiments, the subject is suffering from cholera.

DETAILED DESCRIPTION OF THE INVENTION

Dehydration has many causes. Dehydration may result from prolonged physical activity, acute diarrhea (usu. caused by infection with a pathogen such as *Vibrio cholerae, Campylobacter jejuni*, and *Giardia lamblia*), prolonged exposure to dry air, blood loss or hypotension due to physical trauma, diarrhea, hyperthermia, shock, vomiting, burns, lacrimation, use of drugs (e.g., methamphetamine, amphetamine, caffeine and other stimulants), excessive consumption of alcoholic beverages, malnutrition, electrolyte disturbance, fasting, severe hyperglycemia (especially in diabetes mellitus), glycosuria, uremia, and diabetes insipidus. Acute diarrhea is a worldwide problem. The loss of fluids through diarrhea may result in dehydration and electrolyte imbalances. Dehydration due to acute diarrhea is a common cause of death in developing countries and the second most common cause of infant deaths worldwide. In 2009, dehydration due to acute diarrhea was estimated to have caused 1.1 million deaths in people aged 5 and over and 1.5 million deaths in children under the age of 5. There is a need for an effective treatment for dehydration. Such treatment is preferably easy to administer (e.g., by a non-medical professional). Such treatments should also be easily distributable, portable, compact and with an extended shelf life (e.g., to facilitate distribution to developing countries and storage by hospitals, clinics or subjects). The presently disclosed compositions fulfill these, and additional, needs.

The human body's ability to absorb water and ions results from two opposing, unidirectional fluxes of ions, one absorptive and the other secretory. The two processes are anatomically separated: absorption takes place mainly in the mature villous cells, whereas secretion seems to occur in the crypt cells. The absorption of water and nutrients is dependent on the osmotic gradient dictated by sodium transport via the following three mechanisms: neutral NaCl absorption, sodium absorption coupled to the absorption of organic solutes (such as, glucose and amino acids), and electrogenic sodium absorption. In normal circumstances, absorptive processes for water and electrolytes prevail over secretory processes and as a result, water is absorbed. In certain instances (e.g., prolonged exercise or diarrheal diseases), the balance of absorption and secretion is disturbed and dehydration may result. In diarrheal disease, neutral NaCl absorption and electrogenic sodium absorption are disturbed; however, sodium absorption coupled to the absorption of organic solutes appears to be unaffected.

Glucose is an organic solute that promotes in sodium transport. Sodium-dependent glucose cotransporter proteins are found in the intestinal mucosa of the small intestine. These proteins use the energy from a downhill sodium gradient to transport glucose across the apical membrane against an uphill glucose gradient. The sodium-dependent glucose cotransporter proteins transport both sodium and glucose in the same direction across the membrane.

Current Treatments

The preservation of the sodium/organic solute transport mechanism was the rationale behind the development of the current oral rehydration salt (ORS) therapies.

In 1975, the WHO first introduced ORS therapy. The first WHO ORS had an osmolarity of 311 mOsm/L and concentrations of sodium at 90 mEq/L, potassium at 20 mEq/L, chloride at 80 mEq/L and glucose at 20 g/L. The current WHO ORS formulation has an osmolarity of 245 mOsm/L and concentrations of sodium at 75 mEq/L, potassium at 20 mEq/L, chloride at 65 mEq/L and glucose at 13.5 g/L. The WHO guidelines also teach that, in general, glucose concentration should equal the sodium concentration and sodium should be within the range of 60-90 mEq/L.

Studies have shown that reduced osmolarity ORS results in increased water absorption when compared with standard WHO ORS. The effectiveness and complications of reduced-osmolarity ORS (osmolarity less than 250 mOsm/L) has been compared with those of the standard WHO-ORS. These studies have shown that reduced osmolarity ORS result in decreases in stool output, episodes of vomiting and need for intravenous hydration. The current WHO ORS protocol has an osmolarity of 245 mOsm/L. Studies have indicated that the osmolarity of the current WHO standard formulation may still be too high and thus may result in excessive stool output, episodes of vomiting and need for intravenous hydration. Thus, there is a need for an ORS with a greater reduction in osmolarity.

Due to the preservation of the glucose/sodium co-transport pathways, the standard WHO ORS protocol utilizes glucose as the organic solute. Multiple studies have demonstrated that glucose is the optimal solute for an ORS. Some studies have suggested that alternative sugars may be used in addition to glucose or even substituted for glucose; however, there has been no consensus amongst the studies that the substitution of alternative sugars for glucose results in an increase in efficacy. In fact, multiple studies have shown that substituting alternative sugars (e.g., sucrose) for glucose results in decreased efficacy. For example, substitution of sucrose for glucose results in loss of efficacy and increased failure rates (11.5% for the sucrose-containing solution group and 7.3% for the glucose-containing group; Black, et al., Glucose vs sucrose in oral rehydration solutions for infants and young children with rotavirus-associated diarrhea). Studies have also shown that substituting sucrose for glucose results in decreased salt and water absorption (Dias, et al., Improving the palatability of oral rehydration solutions has implications for salt and water transport: a study in animal models). Additional studies have shown that substituting sucrose for glucose results in increase stool output.

Neither WHO formulation helps to reduce the volume of stool and duration of diarrhea. Further, both formulations have a level of sodium that is too high for children and adults that are not considered malnourished. There is a need for an oral rehydration solution that (a) reduces stool volume and duration of diarrhea, and (b) has a decreased sodium concentration. The presently disclosed compositions fulfill this need.

Oral Rehydration Compositions

Disclosed herein, in certain embodiments, are oral rehydration compositions for use in treating or preventing dehydration comprising (a) at least 25% w/w of carbohydrate, and (b) at least one electrolyte. Further disclosed herein, in certain embodiments, are oral rehydration solutions for use in treating or preventing dehydration comprising (a) at least 30 g/L of carbohydrate, and (b) at least one electrolyte. In some embodiments, the oral rehydration composition is a solid. In some embodiments, the oral rehydration composition is an oral rehydration solution. In some embodiments, the oral rehydration composition is a solid that is mixed with a suitable amount of a suitable liquid (e.g., water) to form an oral rehydration solution.

Sugars

Disclosed herein, in certain embodiments, are oral rehydration compositions for use in treating or preventing dehydration comprising: (a) at least one carbohydrate, and (b) at least one electrolyte.

In some embodiments, the at least one carbohydrate is sucrose, Sucrose is a disaccharide consisting of fructose bound by a glycosidic linkage to glucose in a 1:1 ratio. Gastric acidity during digestion induces hydrolysis of the glycosidic bonds, converting sucrose into glucose and fructose.

In the small intestine, glucose molecules derived from sucrose activate the glucose/sodium co-transport pathway resulting in water and sodium absorption. Additionally, the fructose molecules derived from sucrose may also support water and sodium absorption. It appears that fructose may promote sodium transport in the small intestine, possibly by increasing the abundance of the sodium/phosphate co-transporter. Studies indicate that fructose stimulates 66-100% as much net sodium and water absorption as glucose. Additionally, studies demonstrate that fructose stimulates potassium absorption, whereas glucose stimulates potassium secretion. This combination of glucose/sodium co-transport and sodium/phosphate co-transport results in increased water and sodium absorption as compared to an ORS made of glucose or fructose. Further, studies indicate that the 1:1 ratio of glucose to fructose results in a higher absorption than any other ratio of glucose to fructose. See, e.g., Fujisawa, T; Riby J, Kretchmer N (1991). "Intestinal absorption of fructose in the rat". Gastroenterology 101: 360-367.

In some embodiments, an oral rehydration composition disclosed herein comprises at least 25% w/w sucrose, at least 30% w/w sucrose, at least 40% w/w sucrose, at least 45% sucrose, at least 46% w/w sucrose, or at least 47% w/w sucrose. In some embodiments, an oral rehydration composition disclosed herein comprises at least 48% w/w sucrose. In some embodiments, an oral rehydration composition disclosed herein comprises about 48% w/w sucrose. In some embodiments, an oral rehydration composition disclosed herein comprises at least 700 mmol/L sucrose, at least 800 mmol/L sucrose, at least 900 mmol/L sucrose, at least 1000 mmol/L sucrose, at least 1100 mmol/L sucrose, at least 1200 mmol/L sucrose, at least 1300 mmol/L sucrose, or at least 1400 mmol/L sucrose. In some embodiments, an oral rehydration composition disclosed herein comprises about 1400 mmol/L sucrose. In some embodiments, an oral rehydration composition disclosed herein comprises at least 10 g sucrose, 15 g sucrose, 20 g sucrose, at least 20.2 g sucrose, 21 g sucrose, 22 g sucrose, 23 g sucrose, 24 g sucrose, 25 g sucrose, 26 g sucrose, 27 g sucrose, 28 g sucrose, 29 g sucrose, 30 g sucrose, 35 g sucrose, or 40 g sucrose.

Alternatively, in some embodiments, the at least one carbohydrate is glucose, fructose or combination thereof In some embodiments, the composition comprises at least 25% w/w glucose and fructose, at least 30% w/w glucose and fructose, at least 40% w/w glucose and fructose, at least 45% w/w glucose and fructose, at least 46% w/w glucose and fructose, or at least 47% w/w glucose and fructose. In some embodiments, the compositions comprises 25% w/w glucose and fructose in a 1:1 ratio of glucose to fructose, at least 30% w/w glucose and fructose in a 1:1 ratio of glucose to fructose, at least 40% w/w glucose and fructose in a 1:1 ratio of glucose to fructose, at least 45% w/w glucose and fructose in a 1:1 ratio of glucose to fructose, at least 46% w/w glucose and fructose in a 1:1 ratio of glucose to fructose, or at least 47% w/w glucose and fructose in a 1:1 ratio of glucose to fructose. In some embodiments, the composition comprises at least 48% w/w glucose and fructose. In some embodiments, the composition comprises about 48% w/w glucose and fructose in a 1:1 ratio of glucose to fructose. In some embodiments, the composition comprises between 1000 and 2000 mmol/L glucose and between 1000 and 2000 mmol/L fructose. In some embodiments, the composition comprises between 1200 and 1800 mmol/L glucose and between 1200 and 1800 mmol/L fructose. In some embodiments, the composition comprises between 1300 and 1500 mmol/L glucose and between 1300 and 1500 mmol/L fructose. In some embodiments, the composition comprises between 1300 and 1400 mmol/L glucose and between 1300 and 1400 mmol/L fructose. In some embodiments, the composition comprises between 1300 and 1350 mmol/L glucose and between 1300 and 1350 mmol/L fructose. In some embodiments, the composition comprises about 1330 mmol/L glucose and about 1330 mmol/L fructose.

In some embodiments, the carbohydrate is sucrose, glucose, fructose, or any combination thereof In some embodiments, the composition comprises less than 0.5% w/w glucose, less than 0.1% w/w glucose, less than 0.05% w/w glucose, or less than 0.001% w/w glucose. In some embodiments, the composition comprises less than 0.56 mmol/L glucose, less than 2.8 mmol/L glucose, less than 5.6 mmol/L glucose, or less than 27.8 mmol/L glucose. In some embodiments, the composition comprises at least 5% w/w fructose, at least 10% w/w fructose, at least 11% w/w fructose, at least 12% w/w fructose, at least 13% w/w fructose, at least 14% w/w fructose, at least 15% w/w fructose, at least 16% w/w fructose, at least 17% w/w fructose, at least 18% w/w fructose, at least 19% w/w fructose, or at least 20% w/w fructose. Any of the above embodiments may have sucrose and fructose, but no glucose.

In some embodiments, an oral rehydration composition disclosed herein comprises a ratio of sucrose to fructose of about 1:1, about 2:1, about 3:1, about 4:1, or about 5:1.

In some embodiments, an oral rehydration composition disclosed herein comprises at least 1 g fructose, at least 1.5 g fructose, at least 2 g fructose, at least 2.1 g fructose, at least 2.2 g fructose, at least 2.3 g fructose, at least 2.4 g fructose, at least 2.5 g fructose, at least 2.6 g fructose, at least 2.7 g fructose, at least 2.8 g fructose, at least 2.9 g fructose, at least 3.0 g fructose, at least 3.5 g fructose, at least 4.0 g fructose, at least 4.5 g fructose, at least 5 g fructose, at least 5.1 g fructose, at least 5.2 g fructose, at least 5.3 g fructose, at least 5.4 g fructose, at least 5.5 g fructose, or at least 6 g fructose.

In some embodiments, the at least one carbohydrate is sucrose, glucose, fructose, dextrose, rice starch, maltodextran, or any combination thereof. In some embodiments, the carbohydrate is rice starch (e.g. rice flour or rice syrup). In some embodiments, the carbohydrate is maltodextran. In some embodiments, the carbohydrate is dextrose.

Electrolytes

Disclosed herein, in certain embodiments, are oral rehydration compositions (e.g., solution or solids) for use in treating or preventing dehydration. Such compositions can include one or more electrolytes. The electrolytes are preferably at a concentration of less than 30% w/w, 20% w/w, 19% w/w, 18% w/w, 17% w/w, 16% w/w, 15% w/w, 14% w/w, 13% w/w, 12% w/w, 11% w/w, 10% w/w, 9% w/w, 8% w/w, 7% w/w or 5% w/w. In some instances, a composition comprises (a) at least 25% w/w of sucrose, or glucose and fructose, and (b) at least one electrolyte. In some embodiments, a composition disclosed here comprises one, two, three, four, five, six, or seven electrolytes. In some embodiments, a composition disclosed herein comprises at least one of sodium, potassium, calcium, magnesium, chloride, hydrogen phosphate, or hydrogen carbonate. In some embodiments, a composition disclosed herein comprises at least two of sodium, potassium, calcium, magnesium, chloride, hydrogen phosphate, or hydrogen carbonate. In some embodiments, a composition disclosed herein comprises at least three of sodium, potassium, calcium, magnesium, chloride, hydrogen phosphate, or hydrogen carbonate. In some embodiments, a composition disclosed herein comprises at least four of sodium, potassium, calcium, magnesium, chloride, hydrogen phosphate, or hydrogen carbonate. In some embodiments, a composition disclosed herein comprises at least five of sodium, potassium, calcium, magnesium, chloride, hydrogen phosphate, or hydrogen carbonate. In some embodiments, a composition disclosed herein comprises at least six of sodium, potassium, calcium, magnesium, chloride, hydrogen phosphate, or hydrogen carbonate. In some embodiments, a composition disclosed herein comprises at least seven of sodium, potassium, calcium, magnesium, chloride, hydrogen phosphate, or hydrogen carbonate.

In some embodiments, an oral rehydration composition disclosed herein comprises less than 12.5% w/w sodium, less than 10% w/w sodium, less than 5% w/w sodium, less than 4% w/w sodium, less than 3.5% w/w sodium, less than 3% w/w sodium, less than 2.5% w/w sodium, or less than 1% w/w sodium. In some embodiments, an oral rehydration composition disclosed herein comprises between about 3% w/w sodium and 3.5% w/w sodium. In some embodiments, an oral rehydration composition disclosed herein comprises about 3% w/w sodium, about 3.1% w/w sodium, about 3.2% w/w sodium, about 3.3% w/w sodium, about 3.4% w/w sodium, or about 3.5% w/w sodium.

In some embodiments, an oral rehydration composition disclosed herein comprises less than about 75 mmol/L sodium, less than about 60 mmol/L sodium, less than about 50 mmol/L sodium, less than about 40 mmol/L sodium, less than about 35 mmol/L sodium, less than about 30 mmol/L sodium, less than about 25 mmol/L sodium, less than about 20 mmol/L sodium, less than about 15 mmol/L sodium, or less than about 10 mmol/L sodium. In some embodiments, an oral rehydration composition disclosed herein comprises between about 70 mmol/L sodium and about 50 mmol/L sodium. In some embodiments, an oral rehydration composition disclosed herein comprises less than about less than about 70 mmol/L sodium, less than about 69 mmol/L sodium, less than about 68 mmol/L sodium, less than about 67 mmol/L sodium, less than about 66 mmol/L sodium, less than about 65 mmol/L sodium, less than about 64 mmol/L sodium, less than about 63 mmol/L sodium, less than about 62 mmol/L sodium, less than about 61 mmol/L sodium, less than about 60 mmol/L sodium, less than about 59 mmol/L sodium, less than about 58 mmol/L sodium, less than about 57 mmol/L sodium, less than about 56 mmol/L sodium, or less than about 55 mmol/L sodium. In some embodiments, an oral rehydration composition disclosed herein comprises about 60 mmol/L sodium. In some embodiments, an oral rehydration composition disclosed herein comprises about 58 mmol/L sodium. In some embodiments, an oral rehydration composition disclosed herein comprises about 57 mmol/L sodium In some embodiments, an oral rehydration composition disclosed herein comprises less than 2.5% w/w chloride, less than 2% w/w chloride, less than 1.5% w/w chloride, less than 1% w/w chloride, less than 0.9% w/w chloride, less than 0.8% w/w chloride, less than 0.7% w/w chloride, less than 0.6% w/w chloride, less than 0.5% w/w chloride, less than 0.4% w/w chloride, less than 0.3% w/w chloride, less than 0.2% w/w chloride, or less than 0.1% w/w chloride. In some embodiments, an oral rehydration composition disclosed herein comprises less than 0.69% w/w chloride, less than 0.68% w/w chloride, less than 0.67% w/w chloride, less than 0.66% w/w chloride, less than 0.65% w/w chloride, less than 0.64% w/w chloride, less than 0.63% w/w chloride, less than 0.62% w/w chloride, or less than 0.61% w/w chloride. In some embodiments, an oral rehydration composition disclosed herein comprises about 0.6% w/w chloride.

In some embodiments, an oral rehydration composition disclosed herein comprises less than 90 mmol/L chloride, less than 78 mmol/L chloride, less than 77 mmol/L chloride, less than 76 mmol/L chloride, less than 75 mmol/L chloride, less than 61 mmol/L chloride, less than 60 mmol/L chloride, less than 50 mmol/L chloride, less than 40 mmol/L chloride, less than 31 mmol/L chloride, less than 30 mmol/L chloride, less than 25 mmol/L chloride, less than 17 mmol/L chloride, less than 16 mmol/L chloride, less than 15 mmol/L chloride, less than 14 mmol/L chloride, less than 13 mmol/L chloride, less than 12 mmol/L chloride, less than 11 mmol/L chloride, less than 10 mmol/L chloride, less than 9 mmol/L chloride, less than 8 mmol/L chloride; less than 6 mmol/L chloride, less than 5 mmol/L chloride, less than 4 mmol/L chloride, less than 3 mmol/L chloride, less than 2 mmol/L chloride, or less than 1 mmol/L chloride. In some embodiments, an oral rehydration composition disclosed herein comprises less than 8 mmol/L chloride, less than 7.9 mmol/L chloride, or less than 7.8 mmol/L chloride. In some embodiments, an oral rehydration composition disclosed herein comprises less than 3.99 mmol/L chloride, less than 3.98 mmol/L chloride, less than 3.97 mmol/L chloride, less than 3.96 mmol/L chloride, less than 3.95 mmol/L chloride, less than 3.94 mmol/L chloride, less than 3.93 mmol/L chloride, less than 3.92 mmol/L chloride, or less than 3.91 mmol/L chloride. In some embodiments, an oral rehydration composition disclosed herein comprises about 7.8 mmol/L chloride. In some embodiments, an oral rehydration composition disclosed herein comprises about 3.9 mmol/L chloride.

In some embodiments, an oral rehydration composition disclosed herein comprises a ratio of sodium to chloride of at least 1.5:1, at least 2:1, at least 2.5:1, at least 3:1, at least 3.5:1, at least 4:1, at least 4.5:1, at least 5:1, at least 5.5:1, at least 6:1, at least 6.5:1, at least 7:1, at least 7.5:1, at least 8:1, at least 8.5:1, at least 9:1, at least 9.5:1, or at least 10:1. In some embodiments, an oral rehydration composition disclosed herein comprises a ratio of sodium to chloride of 7:1.

In some embodiments, an oral rehydration composition disclosed herein comprises potassium. In some embodiments, an oral rehydration composition disclosed herein comprises less than 5% w/w potassium, less than 4% w/w potassium, less than 3% w/w potassium, less than 2% w/w potassium, less than 1% w/w potassium, or less than 0.5% w/w potassium. In some embodiments, an oral rehydration composition disclosed herein comprises between about 1.8% and about 1.9% w/w potassium.

In some embodiments, an oral rehydration composition disclosed herein comprises less than 21 mmol/L potassium, less than 16 mmol/L potassium, less than 11 mmol/L potassium, or less than 6 mmol/L potassium. In some embodiments, an oral rehydration composition disclosed herein comprises less than 50 mmol/L potassium, less than 40 mmol/L potassium, less than 35 mmol/L potassium, less than 25 mmol/L potassium, less than 20 mmol/L potassium, less than 15 mmol/L potassium, less than 10 mmol/L potassium, or less than 5 mmol/L potassium. In some embodiments, an oral rehydration composition disclosed herein comprises about 10.1 mmol/L potassium.

In some embodiments, an oral rehydration composition disclosed herein comprises calcium. In some embodiments, an oral rehydration composition disclosed herein comprises less than 5% w/w calcium, less than 4% w/w calcium, less than 3% w/w calcium, less than 2% w/w calcium, less than 1% w/w calcium, less than 0.5% w/w calcium, less than 0.1% w/w calcium, less than 0.05% w/w calcium, or less than 0.01% w/w calcium. In some embodiments, an oral rehydration composition disclosed herein comprises about 0.01% w/w calcium.

In some embodiments, an oral rehydration composition disclosed herein comprises less than 2.5 mmol/L calcium, less than 12.5 mmol/L calcium, less than 25 mmol/L calcium, less than 125 mmol/L calcium, less than 250 mmol/L calcium, less than 500 mmol/L calcium, less than 750 mmol/L calcium, less than 1000 mmol/L calcium, or less than 1250 mmol/L calcium. In some embodiments, an oral rehydration composition disclosed herein comprises about 2.5 mmol/L calcium.

In some embodiments, an oral rehydration composition disclosed herein comprises magnesium. In some embodiments, an oral rehydration composition disclosed herein comprises less than 10% w/w magnesium, less than 5% w/w magnesium, less than 2% w/w magnesium, less than 1% w/w magnesium, or less than 0.5% w/w magnesium. In some embodiments, an oral rehydration composition disclosed herein comprises about 3.9% w/w magnesium.

In some embodiments, an oral rehydration composition disclosed herein comprises less than 10 mmol/L magnesium, less than 5 mmol/L magnesium, less than 4 mmol/L magnesium, less than 3 mmol/L magnesium, less than 2 mmol/L magnesium, or less than 1 mmol/L magnesium. In some embodiments, an oral rehydration composition disclosed herein comprises about 1.7 mmol/L magnesium.

In some embodiments, an oral rehydration composition disclosed herein comprises hydrogen phosphate, hydrogen carbonate, or a combination thereof Osmolarity Disclosed herein, in certain embodiments, are oral rehydration compositions (for use in treating or preventing dehydration comprising a sugar and at least one electrolyte. In some embodiments, the oral rehydration composition is a solid. In some embodiments, the oral rehydration composition is an oral rehydration solution. In some embodiments, the oral rehydration composition is a solid that is mixed with a suitable amount of a suitable liquid (e.g., water) to form an oral rehydration solution. In some embodiments, an oral rehydration solution disclosed herein is a "reduced osmolarity" solution. In some embodiments, an oral rehydration solution disclosed herein comprises an osmolarity between 200 mOsm/L and 270 mOsm/L.

In some embodiments, an oral rehydration solution disclosed herein comprises an osmolarity of less than 275 mOsm/L, less than 270 mOsm/L, less than 260 mOsm/L, less than 250 mOsm/L, less than 240 mOsm/L, less than 235 mOsm/L, less than 230 mOsm/L, less than 225 mOsm/L, less than 220 mOsm/L, less than 215 mOsm/L, less than 210 mOsm/L, less than 205 mOsm/L, or less than 200 mOsm/L. In some embodiments, an oral rehydration composition disclosed herein comprises an osmolarity of less than 239 mOsm/L, less than 238 mOsm/L, less than 237 mOsm/L, less than 236 mOsm/L, less than 235 mOsm/L, less than 234 mOsm/L, less than 233 mOsm/L, less than 232 mOsm/L, less than 231 mOsm/L, less than 230 mOsm/L, less than 225 mOsm/L, less than 220 mOsm/L, less than 215 mOsm/L, less than 210 mOsm/L, less than 205 mOsm/L, less than 200 mOsm/L, less than 195 mOsm/L, less than 190 mOsm/L, less than 185 mOsm/L, less than 180 mOsm/L, less than 170 mOsm/L, less than 160 mOsm/L, less than 150 mOsm/L, less than 140 mOsm/L, less than 135 mOsm/L, less than 130 mOsm/L, less than 125 mOsm/L, less than 120 mOsm/L, less than 115 mOsm/L, less than 110 mOsm/L, or less than 100 mOsm/L. In some embodiments, an oral rehydration composition disclosed herein comprises an osmolarity of between about 234 to about 237 mOsm/L.

Citric Acid and Citrate

In some embodiments, an oral rehydration composition disclosed herein further comprises citric acid, citrate, or a combination thereof. In some embodiments, citrate or citric acid promotes cleavage of sucrose in the stomach and upper small intestine. In some embodiments, cleavage of sucrose in the stomach and small intestine results in the upper jejunum preferentially absorbing the cleaved glucose and fructose, delivering them to the hepatic portal vein.

In some embodiments, an oral rehydration composition disclosed herein comprises less than 50% w/w citric acid or citrate, less than 40% w/w citric acid or citrate, less than 30% w/w citric acid or citrate, less than 25% w/w citric acid or citrate, less than 20% w/w citric acid or citrate, less than 15% w/w citric acid or citrate, less than 10% w/w citric acid or citrate, less than 5% w/w citric acid or citrate, or less than 1% w/w citric acid or citrate. In some embodiments, an oral rehydration composition disclosed herein comprises about 25% w/w citric acid or citrate. In some embodiments, an oral rehydration composition disclosed herein further comprises less than 200 meq/L citric acid or citrate, less than 180 meq/L citric acid or citrate, less than 160 meq/L citric acid or citrate, less than 150 meq/L citric acid or citrate, less than 140 meq/L citric acid or citrate, less than 130 meq/L citric acid or citrate, less than 120 meq/L citric acid or citrate, less than 110 meq/L citric acid or citrate, or less than 100 meq/L citric acid or citrate. In some embodiments, an oral rehydration composition disclosed herein further comprises between about 170 meq/L citric acid or citrate and 130 meq/L citric acid or citrate. In some embodiments, an oral rehydration composition disclosed herein further comprises between about 165 meq/L citric acid or citrate and 135 meq/L citric acid or citrate.

Miscellaneous Ingredients

In some embodiments, an oral rehydration composition disclosed herein further comprises a coloring agent, preserving agent, or flavoring agent. In some embodiments, the flavoring agent is selected from: acacia syrup, acesulfame K, alitame, anise, apple, aspartame, banana, Bavarian cream, berry, black currant, butterscotch, calcium citrate, camphor, caramel, cherry, cherry cream, chocolate, cinnamon, bubble gum, citrus, citrus punch, citrus cream, cotton candy, cocoa, cola, cool cherry, cool citrus, cyclamate, cylamate, dextrose, eucalyptus, eugenol, fructose, fruit punch, glycyrrhetinate, glycyrrhiza (licorice) syrup, grape, grapefruit, honey, isomalt, lemon, lime, lemon cream, monoammonium glyrrhizinate (MagnaSweet®), maltol, mannitol, maple, marshmallow, menthol, mint cream, mixed berry, neohesperidine DC, neotame, orange, pear, peach, peppermint, peppermint cream, Prosweet® Powder, raspberry, root beer, rum, saccharin, safrole, sorbitol, spearmint, spearmint cream, strawberry, strawberry cream, stevia, sucralose, sucrose, sodium saccharin, saccharin, aspartame, acesulfame potassium, mannitol, talin, sylitol, sucralose, sorbitol, Swiss cream, tagatose, tangerine, thaumatin, tutti fruitti, vanilla, walnut, watermelon, wild cherry, wintergreen, xylitol, or any combination of these flavoring ingredients, e.g., anise-menthol, cherry-anise, cinnamon-orange, cherry-cinnamon, chocolate-mint, honey-lemon, lemon-lime, lemon-mint, menthol-eucalyptus, orange-cream, vanilla-mint, and mixtures thereof. In some embodiments, the flavoring agent is citrus flavor. In some embodiments, the flavoring agent is lemon flavor, lime flovor, lemon-lime flavor, tangerine flavor, orange flavor, or any combination thereof.

In some embodiments, an oral rehydration composition disclosed herein further comprises an amino acid. In some embodiments, an oral rehydration composition disclosed herein further comprises glycine, glycl-glycine, alanine, glutamine, or arginine. In some embodiments, the amino acid is an L amino acid. In some embodiments, the amino acid is a D amino acid. In some embodiments, the amnio acid is L-glutamine or L-alanine.

In some embodiments, an oral rehydration composition disclosed herein further comprises fiber, e.g., cellulose or cellulose derivatives. In some embodiments, a composition further comprises a carboxylated cellulose.

In some embodiments, an oral rehydration composition disclosed herein further comprises an antacid. In some embodiments, an oral rehydration composition disclosed herein further comprises sodium bicarbonate. In some embodiments, an oral rehydration composition disclosed herein further comprises: aluminium hydroxide; magnesium hydroxide; aluminum carbonate; calcium carbonate; hydrotalcite; bismuth subsalicylate; magaldrate; or any combination thereof.

In some embodiments, an oral rehydration composition disclosed herein further comprises a nitrate or any nitrogen ingredient that produces nitric oxide.

Formulations

In some embodiments, an oral rehydration composition disclosed herein is formulated as a solid dosage form or a liquid dosage form. In some embodiments, the solid dosage forms disclosed herein may be in the form of a tablet, (including a suspension tablet, a fast-melt tablet, a bite-disintegration tablet, a rapid-disintegration tablet, an effervescent tablet, or a caplet), a pill, a powder (including a sterile packaged powder, a dispensable powder, or an effervescent powder) a capsule (including both soft or hard capsules, e.g., capsules made from animal-derived gelatin or plant-derived HPMC, or "sprinkle capsules"), solid dispersion, solid solution, bio-erodible dosage form, controlled release formulations, pulsatile release dosage forms, multiparticulate dosage forms, pellets, or granules. In other embodiments, the pharmaceutical formulation is in the form of a powder. In still other embodiments, the pharmaceutical formulation is in the form of a tablet, including but not limited to, a fast-melt tablet. In some embodiments, an oral rehydration composition disclosed herein is formulated as a solution, syrup, or suspension.

In some embodiments, an oral rehydration composition disclosed herein is formulated as a solid dosage form. In some embodiments, the solid dosage form is mixed with a suitable amount of a suitable liquid and administered to a subject in need of rehydration. As used herein, a "suitable liquid" is any liquid that does not deleteriously change the concentration of one or more components of the oral rehydration composition, or the osmotic balance of the oral rehydration composition. As used herein, a "suitable amount" is any amount of a liquid that does not deleteriously change the concentration of one or more components of the oral rehydration composition, or the osmotic balance of the oral rehydration composition. In some embodiments, the solid dosage form is mixed with a suitable amount of water and administered to a subject in need of rehydration. In some embodiments, the solid dosage form is mixed with 250 mL of water and administered to a subject in need of rehydration. In some embodiments, the solid dosage form is mixed with 500 mL of water and administered to a subject in need of rehydration. In some embodiments, the solid dosage form is mixed with 1 L of water and administered to a subject in need of rehydration. In some embodiments, the solid dosage form is mixed with 2 Ls of water and administered to a subject in need of rehydration. In some embodiments, the solid dosage form is mixed with 3 Ls of water and administered to a subject in need of rehydration.

Conventional pharmacological techniques include, e.g., one or a combination of methods: (1) dry mixing, (2) direct compression, (3) milling, (4) dry or non-aqueous granulation, (5) wet granulation, or (6) fusion. See, e.g., Lachman et al., The Theory and Practice of Industrial Pharmacy (1986). Other methods include, e.g., spray drying, pan coating, melt granulation, granulation, fluidized bed spray drying or coating (e.g., wurster coating), tangential coating, top spraying, tableting, extruding and the like.

In some embodiments, an oral rehydration composition disclosed herein further comprises a suitable carrier, diluents, or excipient. For example, wherein the composition is formulated as a tablet, the composition may further comprise a lubricants or glidants. Non-limiting examples of lubricants and glidants include e.g., stearic acid, calcium hydroxide, talc, sodium stearyl fumerate, a hydrocarbon such as mineral oil, or hydrogenated vegetable oil such as hydrogenated soybean oil (Sterotex®), higher fatty acids and their alkali-metal and alkaline earth metal salts, such as aluminum, calcium, magnesium, zinc, stearic acid, sodium stearates, glycerol, talc, waxes, Stearowet®, boric acid, sodium benzoate, sodium acetate, sodium chloride, leucine, a polyethylene glycol (e.g., PEG-4000) or a methoxypolyethylene glycol such as Carbowax™, sodium oleate, sodium benzoate, glyceryl behenate, polyethylene glycol, magnesium or sodium lauryl sulfate, colloidal silica such as Syloid™, Cab-O-Sil®, a starch such as corn starch, silicone oil, a surfactant, and the like.

The compositions disclosed herein may also include dispersing agents, disintegrates, and/or viscosity modulating agents in order to facilitate dispersion of the composition in water. Exemplary agents include, e.g., hydrophilic polymers, electrolytes, Tween® 60 or 80, PEG, polyvinylpyrrolidone (PVP; commercially known as Plasdone®), and the carbohydrate-based dispersing agents such as, for example, hydroxypropyl celluloses (e.g., HPC, HPC-SL, and HPC-L), hydroxypropyl methylcelluloses (e.g., HPMC K100, HPMC K4M, HPMC K15M, and HPMC K100M), carboxymethylcellulose sodium, methylcellulose, hydroxyethylcellulose, hydroxypropylcellulose, hydroxypropylmethylcellulose phthalate, hydroxypropylmethylcellulose acetate stearate (HPMCAS), noncrystalline cellulose, magnesium aluminum silicate, triethanolamine, polyvinyl alcohol (PVA), vinyl pyrrolidone/vinyl acetate copolymer (S630), 4-(1,1,3,3-tetramethylbutyl)-phenol polymer with ethylene oxide and formaldehyde (also known as tyloxapol), poloxamers (e.g., Pluronics F68®, F88®, and F108®, which are block copolymers of ethylene oxide and propylene oxide); and poloxamines (e.g., Tetronic 908®, also known as Poloxamine 908®, which is a tetrafunctional block copolymer derived from sequential addition of propylene oxide and ethylene oxide to ethylenediamine (BASF Corporation, Parsippany, N.J.)), polyvinylpyrrolidone K12, polyvinylpyrrolidone K17, polyvinylpyrrolidone K25, or polyvinylpyrrolidone K30, polyvinylpyrrolidone/vinyl acetate copolymer (S-630), polyethylene glycol, e.g., the polyethylene glycol can have a molecular weight of about 300 to about 6000, or about 3350 to about 4000, or about 7000 to about 5400, sodium carboxymethylcellulose, methylcellulose, polysorbate-80, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, polysorbate-80, sodium alginate, polyethoxylated sorbitan monolaurate, polyethoxylated sorbitan monolaurate, povidone, carbomers, polyvinyl alcohol (PVA), alginates, chitosans, starch, e.g., a natural starch such as corn starch or potato starch, a pregelatinized starch such as National 1551 or Amij el®, or sodium starch glycolate such as Promogel® or Explotab®, a cellulose such as a wood product, methylcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose, a cross-linked starch such as sodium starch glycolate, a cross-linked polymer such as crosspovidone, a cross-linked polyvinylpyrrolidone, alginate such as alginic acid or a salt of alginic acid such as sodium alginate, a clay such as Veegum® HV (magnesium aluminum silicate), citrus pulp, sodium lauryl sulfate, sodium lauryl sulfate in combination starch, and the like.

An oral rehydration composition disclosed herein may also include a diluent. The term "diluent" refers to chemical compounds that are used to dilute the compound of interest prior to delivery. Diluents can also be used to stabilize compounds because they can provide a more stable environment. In certain embodiments, diluents increase bulk of the composition to facilitate compression or create sufficient bulk for homogenous blend for capsule filling. Such compounds include e.g., lactose, starch, mannitol, sorbitol, dextrose, microcrystalline cellulose such as Avicel®; dibasic calcium phosphate, dicalcium phosphate dihydrate; tricalcium phosphate, calcium phosphate; anhydrous lactose, spray-dried lactose; pregelatinized starch, compressible sugar, such as Di-Pac® (Amstar); mannitol, hydroxypropylmethylcellulose, hydroxypropylmethylcellulose acetate stearate, sucrose-based diluents, confectioner's sugar; monobasic calcium sulfate monohydrate, calcium sulfate dihydrate; calcium lactate trihydrate, dextrates; hydrolyzed cereal solids, amylose; powdered cellulose, calcium carbonate; glycine, kaolin; mannitol, sodium chloride; inositol, bentonite, and the like.

A composition disclosed herein may be obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients include, for example, fillers such as sugars, including lactose, sucrose, mannitol, or sorbitol; cellulose preparations such as, for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. If desired, disintegrating agents may be added, such as the cross-linked croscarmellose sodium, polyvinylpyrrolidone, agar, or alginic acid or a salt thereof such as sodium alginate.

Compositions which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

Kits

Disclosed herein, in some embodiments, is a kit for use in treating or preventing dehydration comprising an oral rehydration composition disclosed herein and instructions for using the composition. In some embodiments, the oral rehydration composition is a solid dosage form and the instructions include directions for mixing the solid dosage for with a suitable amount of a suitable liquid. In some embodiments, the instructions include directions for mixing the solid dosage for with 250 mL of water. In some embodiments, the instructions include directions for mixing the solid dosage for with 500 mL of water. In some embodiments, the instructions include directions for mixing the solid dosage for with 1000 mL of water.

In some embodiments, the instructions include recommended daily dosage amounts. In some embodiments, the instructions indicate that a child should consume 1 L to 2 Ls per day of a composition disclosed herein, wherein the composition is a liquid or a solid dosage form that has been mixed with a liquid. In some embodiments, the instructions indicate that an adult should consume 1 L to 4 Ls per day of a composition disclosed herein, wherein the composition is a liquid or a solid dosage form that has been mixed with a liquid.

In some embodiments, the kit comprises an oral rehydration composition disclosed herein packaged in a single use package. In some embodiments, the kit comprises an oral rehydration composition disclosed herein packaged in a multi-use package.

Methods of Treatment

Dehydration

Disclosed herein, in certain embodiments, are methods of treating or preventing dehydration in a subject in need thereof comprising administering or providing an oral rehydration composition (e.g., solution or solid) disclosed herein. As used herein, a "subject" means any mammal, e.g., a human mammal or a non-human mammal (e.g., a primate). In some embodiments, the subject in need thereof is a child. In some embodiments, the subject in need thereof is an adult (e.g., an athlete). In some embodiments, the methods comprise alleviating symptoms of dehydration, for example headaches, vascular headaches, and chronic daily headaches. In some embodiments, the methods comprises treating or preventing a disease, disorder, or condition that is induced by dehydration. For example, in some embodiments, the methods treat or prevent the formation of deep vein thrombosis induced by dehydration.

In some embodiments, dehydration results from physical activity, diarrhea (e.g., acute diarrhea), prolonged exposure to dry air, exposure to excessive heat or excessive cold, blood loss or hypotension due to physical trauma, hyperthermia, shock, vomiting, burns, lacrimation, exposure to radiation, use of drugs (e.g., methamphetamine, amphetamine, caffeine and other stimulants), excessive consumption of alcoholic beverages, malnutrition, electrolyte disturbance, fasting, severe hyperglycemia (especially in diabetes mellitus), glycosuria, uremia, diabetes insipidus, Type 1 diabetes, type 2 diabetes, Sjogren's Syndrome, and pressure ulcers (especially, in patients in long term medical care facilities). In some embodiments, dehydration results from physical activity or diarrhea (e.g., acute diarrhea). In some embodiments, dehydration is caused by prolonged physical activity (e.g., cycling, running, hiking, etc.). In some embodiments, dehydration is caused by infection to a pathogen, for example *Vibrio cholerae, Campylobacter jejuni, Giardia lamblia, Clostridium botulinum, Listeria monocytogenes, Staphylococcus aureus, Salmonella, Shigella, Campylobacter enteritis*. In some embodiments, the dehydration results from a bowel disorder. In some embodiments, the dehydration results from an inflammatory bowel disorder. In some embodiments, the dehydration results from ulcerative colitis, Crohn's disease, IBS, or a combination thereof. In some embodiments, the dehydration results from a bowel preparation (e.g., preparation for a colonoscopy). In some embodiments, dehydration results from cystic fibrosis. In some embodiments, dehydration results from AIDS and/or AIDS wasting syndrome. In some embodiments, dehydration results from hyperemesis gravidarum. In some embodiments, the dehydration results from third spacing (e.g., following a surgical procedure such as liposuction, or due to the presence of burns on the body). In some embodiments, dehydration results from ascites, accumulation of fluid at a burn site, pleural effusion, or a combination thereof.

In some embodiments, the dehydration is classified as mild dehydration (e.g., 3%-5%). Where the dehydration is mild dehydration, in some embodiments, the method comprises administering an oral rehydration composition disclosed herein. In some embodiments, the method comprises administering about 50 mL/kg of an oral rehydration composition disclosed herein for about 4 hours to about 6 hours.

In some embodiments, the dehydration is classified as moderate dehydration (e.g., 6%-9%). Where the dehydration is moderate dehydration, in some embodiments, the method comprises administering an oral rehydration composition disclosed herein. In some embodiments, the method comprises administering about 100 mL/kg of an oral rehydration composition disclosed herein for about 4 hours to about 6 hours. Reevaluation of hydration and management should occur at intervals no greater than 1 hour.

In some embodiments, the dehydration is classified as severe dehydration (e.g., greater than 10%). Where the dehydration is severe dehydration, in some embodiments, the method comprises administering an oral rehydration composition disclosed herein. In some embodiments, the method comprises administering about 20 mL to about 40 mL/kg of an oral rehydration composition disclosed herein for about 30 minutes to about 60 minutes. In some embodiments, the method further comprises administering fluids by iv. Reevaluation of hydration and management should occur at intervals no greater than 1 hour.

In some embodiments, the dehydration is transient dehydration.

In some embodiments, a method of treating dehydration further comprises administering about 10 mL/kg of an oral rehydration composition disclosed herein for each diarrheal stool during the period. In some embodiments, the method further comprises administering an oral rehydration solution disclosed herein in an amount that is approximately equal to the volume of fluid lost due to vomiting.

In some embodiments, a method of treating dehydration further comprises administering IV fluids. In some embodiments, a method of treating dehydration further comprises administering an antimicrobial agent (e.g., an antibacterial agent or an antiviral agent). Typical antimicrobial agents include aminoglycosides, polymyxins, fluoroquinolone, cephalosporins, penicillins, sulfonamides, quinolones, cephems, and penems. In some embodiments, the method further comprises administering tetracycline, kanamycin, streptomycin, ampicillin, kanamycin, tetracycline, gentamicin, erythromycin, Nalidixic Acid, pivmecillinam, Trimethoprim/sulfamethoxazole (TMPSMZ), chloramphenicol, furazolidone, azithromycin, minocycline, ciprofloxacin, erythromycin, doxycycline, neomycin, gentamycin, tobramycin, polymyxin B, ofloxacin and ciprofloxacin, cefuroxime, ceflacor, cefprozil, loracarbef, cefindir, cefixime, cefpodoxime proxetil, cefibuten, ceftriaxone, amoxicillin, amoxicillin-clavulanate, and penicillinase-resistant penicillin.

Leaky Gut Syndrome

Disclosed herein, in certain embodiments, are methods of increasing blood pressure in a subject with leaky gut syndrome comprising administering or providing an oral rehydration composition (e.g., solution or solid) disclosed herein. Further disclosed herein, in certain embodiments, are methods of preventing leaky gut syndrome in a subject without leaky gut syndrome. In some embodiments, the subject is an athlete.

Short Bowel Syndrome

Disclosed herein, in certain embodiments, are methods of treating dehydration in a subject with short bowel syndrome comprising administering or providing an oral rehydration composition (e.g., solution or solid) disclosed herein.

Kidney Stones

Disclosed herein, in certain embodiments, are methods of treating or preventing kidney stones in a subject in need thereof comprising administering or providing an oral rehydration composition (e.g., solution or solid) disclosed herein. In some embodiments, the compositions disclosed herein alkalinize urine and prevent kidney stones.

EXAMPLES

Example 1

Oral Rehydration Composition

A powdered oral rehydration solution is prepared as follows: 10,100 mg of sucrose, 20 mg of glucose, 2540 mg of fructose, 665 mg of sodium, 139 mg of chloride, 390.5 mg of potassium, and 5250 mg of citric acid.

Example 2

Oral Rehydration Solution

A powdered oral rehydration solution is prepared as follows: 10,100 mg of sucrose, 20 mg of glucose, 2540 mg of fructose, 665 mg of sodium, 139 mg of chloride, 390.5 mg of potassium, and 5250 mg of citric acid. The powdered composition is then mixed with 500 mL of water. The composition has an osmolarity of 237 mOsm/L.

Example 3

Treatment of Dehydration Due to Acute Diarrhea

A child with cholera presents at a clinic in Haiti with diarrhea, vomiting, low blood pressure, and rapid pulse. The doctor prescribes (a) NA, (b) iv. fluids and (c) an oral rehydration solution according to example 1 mixed with 500 mL water. The child is discharged after her condition improves. The doctor advises her parents to continue to administer the oral rehydration solution twice per day for 2 weeks. The parents are advised to mix the oral rehydration solution with 500 mL of boiled water. The child fully recovers.

Example 4

Treatment of Dehydration Due to Prolonged Exercise

A cyclist competes in the Giro d'Italia. During the race and at the end of each day, the cyclist mixes the oral rehydration solution according to example 1 with 500 mL of water and drinks the solution. The cyclist suffers no effects from dehydration.

Example 4

Treatment of an Adult with Leaky Bowel

A subject with leaky bowel is suffering from shock and low blood pressure. The subject is administered an oral rehydration solution according to example 1 mixed with 500 mL water. The subject's blood pressure increases. The subject recovers.

Example 5

Treatment of an Adult with History of Kidney Stones

A subject with kidney stones presents. The subject is administered an oral rehydration solution according to example 1 mixed with 500 mL water. The subject's future kidney stone development risk decreases with chronic use of solution.

Example 6

Treatment of an Adult with 3$^{rd}$ Degree Burns

A subject with 3$^{rd}$ degree burns over 40% of his body presents. The subject is suffering from dehydration due to accumulation of fluids around the burns. The subject is administered an oral rehydration solution according to example 1 mixed with 500 mL water. The subject's dehydration decreases.

Example 7

Treatment of an Elderly Adult in a Long Term Care Facility

A elderly adult resides in a long term care facility. The adult experiences dehydration and chronic constipation which results in a decrease in blood pressure. The adults is administered an oral rehydration solution according to example 1 mixed with 500 mL water twice a day for 1 week. Dehydration decreases, constipation decreases, and the blood pressure increases.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An oral rehydration composition, comprising:
    a) at least 40% w/w sucrose;
    b) between 3% w/w and 5% w/w sodium;
    c) between 0.1% w/w chloride and less than 1.5% w/w chloride;
    d) potassium, at a level less than 5% w/w;
    e) between 20% w/w and 30% w/w citric acid or citrate; and
    f) glucose, at a level less than 0.5% w/w;
wherein the composition has a w/w ratio of sodium ions to chloride ions of at least 5:1, and wherein, upon mixture with an effective amount of water, the composition has an osmolarity of between 230 mOsm/L and 240 mOsm/L.

2. The oral rehydration composition of claim 1, comprising between 0.1% w/w and less than 0.8% w/w chloride.

3. The oral rehydration composition of claim 1, comprising about 1400 mmol/L sucrose upon mixture with an effective amount of water.

4. The oral rehydration composition of claim 1, comprising a w/w ratio of sodium ions to chloride ions of at least 7:1.

5. The oral rehydration composition of claim 1, comprising glucose, in an amount less than 0.1% w/w.

6. The oral rehydration composition of claim 1, further comprising fructose, in an amount less than 20% w/w.

7. An oral rehydration composition, comprising:
    a) at least 40% w/w sucrose; and
    b) glucose, at a level less than 0.5% w/w; and
    c) sodium; chloride; potassium; and citric acid or citrate;
wherein the composition has a w/w ratio of sodium ions to chloride ions of at least 5:1; and wherein upon mixture with an effective amount of water, the composition comprises:
i) between 50 meq/L sodium and 70 meq/L sodium;
ii) between 3 mmol/L chloride and less than 10 mmol/L chloride;
iii) potassium, at a concentration less than 35 mmol/L;
iv) between 170 meq/L citric acid or citrate and 130 meq/L citric acid or citrate; and
v) an osmolarity of between 230 mOsm/L and 240 mOsm/L.

8. The oral rehydration composition of claim 1 wherein the composition comprises between 0.1% w/w chloride and 0.7% w/w chloride.

9. The oral rehydration composition of claim 1 wherein the composition comprises between 0.1% w/w chloride and 0.66% w/w chloride.

10. The oral rehydration composition of claim 7 wherein upon mixture with a suitable amount of water, the composition comprises about 7.8 mmol/L chloride.

11. A method of treating dehydration in a subject in need thereof, comprising administering to the subject the composition of claim 1 or 7.

12. The method of claim 11, wherein the subject is an athlete or a child.

13. The method of claim 11, wherein the subject is suffering from diarrhea.

14. The method of claim 11, wherein the subject is suffering from cholera.

\* \* \* \* \*